US005706603A

United States Patent [19]
Bergquist et al.

[11] Patent Number: 5,706,603
[45] Date of Patent: *Jan. 13, 1998

[54] PRODUCTION METHOD FOR CORN WITH ENHANCED QUALITY GRAIN TRAITS

[75] Inventors: Richard Robert Bergquist, El Paso; Douglas Stuart Nubel, Bloomington, both of Ill.; Donald L. Thompson, Raleigh, N.C.

[73] Assignees: E. I. Du Pont de Nemours and Company; Dupont TopCross International, Inc., both of Wilmington, Del.

[ * ] Notice: The term of this patent shall not extend beyond the expiration date of Pat. No. 5,704,160.

[21] Appl. No.: 464,249

[22] Filed: Jun. 5, 1995

Related U.S. Application Data

[63] Continuation of Ser. No. 50,255, May 12, 1993, abandoned, which is a continuation-in-part of Ser. No. 615,839, filed as PCT/US91/07680, Oct. 11, 1991.

[51] Int. Cl.[6] .............................. A01H 1/00; A01H 5/00
[52] U.S. Cl. ........................... 47/58; 47/58; 47/DIG. 1; 800/200; 800/DIG. 56
[58] Field of Search ........................ 800/200, 205; 47/58, DIG. 4; 435/172.3, 172.1

[56] References Cited

U.S. PATENT DOCUMENTS

| | | | |
|---|---|---|---|
| 4,798,735 | 1/1989 | Friedman | 426/578 |
| 5,004,864 | 4/1991 | Robertson et al. | 800/235 |

OTHER PUBLICATIONS

"Grundzuge Der Pflanzenzuchtung", Walter De Gruyter (Ed.), Berin, NY, 1985, pp. 48–78.

Kuckkuck, H. et al, "Fundamentals of Plant Cultivation", 5th Revised and Expanded Edition, Walter De Gruyter, Berlin, NY, 1985.

Alexander, D. E., et al, "Relationship of Kernel Oil Content to Yield in Maize", Crop Science, 8, 272–274, May/Jun. 1968.

Misevic, D. "Population Cross Diallel Among High Oil Populations of Maize", Crop Science, 29, 613–617, 1989.

Alexander, D.E., "High Oil Corn: Breeding and Nutritional Properties", 43rd Annual Corn and Sorghum Research Conference, 1988, pp. 97–105.

Poehlman, J.M., "Breeding Field Crops", 3rd ed., Avi Publishing Co., Westport, CT, 1986. pp. 76–79, 246, 457–460, 469–471, 473–478, 500–502.

Creech, R. et al, "Maize Breeding and Genetics", Walden, D.B., Ed., John Wiley & Sons, NY, Chap. 16, pp. 249–264, 1978.

Ruskova, K., "Effect of Direction of Crossing on Content of Fats, Proteins and Lysine in Maize Grain", Genet. Sel., 7(5), 353–360, 1974.

Glover, D.V. et al, 1987, Corn, In: Nutritional Quality of Cereal Grains: Genetic and Agronomic Improvement, Olson, R.A. et al, Eds., American Society of Agronomy, Madison, Wisconsin, pp. 183–336.

Rooney, L.W. et al, 1987, Food Uses of Whole Corn and Dry-Milled Fractions, In: Corn: Chemistry and Technology, Watson, S. A. et al, Eds., American Association of Cereal Chemists, Inc., St. Paul, MN, pp. 399–429.

Han, Y. et al, "Nutritive Value of High Oil Corn for Poultry", Poultry Science, 66, 103–111, 1987.

Iowa Corn Growers Association, 1989, "Higher Processing Value in 1989 State Fair Open Class Corn and Soybeans", Bulletin, Aug. 27, 1989.

Dudley, J.W., et al, 1974, "Seventy Generations of Selection for Oil and Protein Concentration in the Maize Kernel", In: Seventy Generations of Selection for Oil and Protein in Maize, Dudley, J.W., Ed., Crop Science Society of America, Madison, WI, pp. 181–212.

Silvela, L. et al, 1989, Effect of Selection Intensity and Population Size on Percent Oil in Maize, Zea mays L. Theoretical and Applied Genetics, 78, 298–304.

Wessel-Beaver, L. et al, "Genetic Control of Modified Endosperm Textile in Opaque-2 Maize", Crop Science, 22, 1095–1098 (1982).

Allard, Principles of Plant Breeding, 468 (1960).

Ullrich, S.E. et al,"Inheritance of the Associated Kernel Characters, High Lysine and Shrunken Endosperm, of the Barley Mutant Riso 1508", Crop Science, 18, 828–831 (1978).

Derieux, M. et al, Biological Abstracts, 68(12), p. 7148, Abstract No. 71145 ((1979).

Madej, L.K. et al, Biological Abstracts, 90(12), Abstract No. 130218 (1990).

Rao, V. et al, Biological Abstracts, 80(5), Abstract No. 36759 (1985).

Murty, D.S. et al, Biological Abstracts, 85(7), Abstract No. 68324 (1988).

Alexander et al. (1977) Corn and Corn Improvement: Breeding Special Industrial and Nutritional Types. ASA publication #18, second edition. p. 363.

Primary Examiner—Gary Benzion
Attorney, Agent, or Firm—Bruce W. Morrissey

[57] ABSTRACT

A novel method of producing corn grain with enhanced quality traits including high oil content has been developed. Through pollination of male-sterile hybrid corn plants by nonisogenic corn plants possessing genes which control the expression of enhanced quality grain traits, grain is obtained possessing such traits much higher than would be expected for self- or cross-pollination. This method can be practiced by farmers using currently accepted farming practices to directly obtain high yields of high-oil corn grain, high-protein corn grain, and other valuable grain for animal feed and other products.

22 Claims, No Drawings

PRODUCTION METHOD FOR CORN WITH ENHANCED QUALITY GRAIN TRAITS

CROSS-REFERENCE TO RELATED APPLICATION

This is a division of application Ser. No. 08/050,225 filed May 12, 1993, now abandoned, which is a continuation-in-part of copending U.S. patent application Ser. No. 07/615,839, filed as PCT/US91/07680 Oct. 11, 1991.

FIELD OF THE INVENTION

This invention teaches a novel method of corn grain production wherein female corn planes, obtained from a high-yielding variety, are grown with and pollinated by nonisogenic corn plants possessing genes which control the expression of enhanced quality grain traits. Following this pollination, grain harvested from the female planes unexpectedly exhibit enhanced quality traits compared to those obtained following self- or cross-pollination of male-fertile or male-sterile versions of the female hybrid.

BACKGROUND OF THE INVENTION

Corn is a major crop used as a human food source, an animal feed, and as a source of carbohydrate, oil, protein, and fiber. It is principally used as an energy source in animal feeds, or as a raw material for recovery of starch, protein feed fractions, fiber, flaking grits, flour, and oil. The number of produces produced from corn or components extracted from corn are numerous, and include, among others, paper sizings, high fructose corn syrup, adhesives, food thickeners, industrial and medical absorbants, and ethanol (from starch); animal feed and feed components (from whole grain, corn silage, corn gluten feed and meal), and corn oil which is extracted from the germ.

Virtually all commercial corn produced in United States, Canada, and Europe, and much of the corn produced in South America, is produced from hybrid seed. The production of corn hybrids requires the development of elite corn inbred lines that demonstrate good general and specific combining ability in order that they produce agronomically superior hybrids. Among traits that plant breeders select for in producing hybrids are high yield potential, good stalk strength, resistance to specific diseases, reasonable drought tolerance, rapid dry down, and grain quality sufficient to allow storage and shipment to market with minimum loss. The development of these elite inbreds is both labor and capital intensive, requiring many years of evaluation in many different environments. The incorporation of additional traits further enhancing grain quality would place additional constraints on plant breeder, dramatically increasing both the time and cost of producing these quality grain inbreds.

Once elite inbreds have been developed, they may be used in several ways no produce commercial hybrid seed. The majority of hybrid seed produced in United States is of the single cross type. Two inbred lines are intermated to give rise to what is termed an F1 single cross hybrid (A X B). In some instances, female parent in the cross is itself an F1 hybrid, so that a three-way cross hybrid is produced with genotype of (A X B) X C. More rarely, a four-way cross hybrid is produced, with both male and female parents as F1 hybrids, resulting in a genotype of (A X B) X (C X D). In all cases, the resulting kernels from this intermating are sold as seed to commercial growers who ultimately harvest F2 grain from the crop for on farm use or commercial sale. A general review of these systems is available in several texts (e.g., Poehlman, J. M., 1987, Breeding Field Crops, 3rd Edition, Avi Publishing Company, Westport, Conn.).

In addition to possessing the proper combination of genetic factors to produce elite hybrids, the inbreds themselves must be reasonably vigorous to support the demands of modern seed production. This can be illustrated by a description of how single cross hybrids are produced commercially. To control the direction of pollination and assure the harvest of predominantly hybrid seed, seed production fields are typically designed so that 4 rows of inbred corn plants serving as females alternate with 1 row of inbred corn planes serving as males, although other planting patterns are possible. The female planes are rendered male sterile either by detasseling, or via genetic mechanisms such as cytoplasmic male sterility which renders the tassel nonfunctional. Ovules borne on these female planes are then fertilized by pollen produced by the male plants, and the resulting hybrid seed borne on the female planes is harvested, cleaned, sized, and treated prior to sale to commercial growers. To produce this hybrid seed economically the male inbred plants need to reliably shed sufficient pollen to fertilize the female plants over a variety of climatic conditions. The hybrid seed borne on the female inbred plants need to be of high quality to allow good germination and early plant vigor in the commercial grower's field, and the female plants themselves need to stand and retain ears until the time of harvest. These requirements of the inbred lines themselves further increase the time and money required to produce commercially successful hybrids.

Thus, the capital- and time-intensive development and testing of inbreds is key to modern corn production. There are three breeding schemes commonly used to produce inbred lines of corn: the pedigree system of breeding, backcross conversion, and recurrent selection. In a commonly practiced form of the pedigree method, two inbred lines of corn, often with different sets of desirable characteristics, are intermated, and superior plants are selected and selfed in succeeding generations to become increasingly inbred. Part of this selection procedure involves a periodic assessment of the performance of the emerging inbred lines in various hybrid combinations. The process of continued selfing and selection, typically over five to eight generations, results in the production of lines which are, to a significant degree, genetically homogeneous or inbred. Development and commercial production of an elite inbred by this method typically takes from 5 to 7 years.

In the second method of breeding, backcross conversion, a desired characteristic (generally, one which is simply inherited, such as certain disease resistances) is introduced into a target elite inbred (the recurrent parent) by intermating the recurrent parent with a source plant expressing a particular trait of interest. This source plant may also be an inbred, but in the broadest sense can be a member of any plant variety or population cross-fertile with the recurrent parent. The progeny of this cross are then back crossed (and sometimes selfed) to the recurrent parent, desirable progeny identified, and the cycle is repeated. After five to eight cycles of backcrossing and selection, this procedure results in the recovery of the desired characteristic in what is substantially genetic background of the recurrent, elite patent. Oftentimes the "converted" inbred can be recovered and produced quickly (three to five years), but since the end product is essentially an "older" line in many respects, backcross conversion is generally considered to be a conservative method of inbred development.

The third method of inbred development, recurrent selection, generally involves the extraction of a new inbred from a broad, genetically heterogeneous breeding pool, commonly termed a population. Individual plants within the population are selected for traits of interest such as stalk strength or combining ability and intermated to create a new population from which again select and intermate individuals with these desired characteristics. Because the number of possible genetic combinations within these populations is quite large, substantial opportunity exists for recovering subpopulations and eventually inbreds with novel grain, seed, or whole plant characteristics. However, an inevitable consequence of this genetic diversity is it takes substantially longer to develop elite inbreds by recurrent selection than by the preceding methods.

In summary, all three of the currently available strategies are labor and capital intensive, each requiring many years of effort to allow for both recombination of genetic information and selection eventually produce elite inbred lines which would efficiently combine to yield hybrid seed which would be sown to produce grain. The rapidity with which satisfactory inbred lines can be developed is determined to a large degree by the nature and number of traits that the lines must possess. The addition of novel or unusual traits, especially if they are controlled by several genes, would significantly increase the time and effort required to produce the desired lines.

Most corn grain is handled as a commodity, since many of the industrial and animal feed requirements for corn can be met by common varieties of field corn which are widely grown and produced in volume. However, there exists at present a growing market for corn with special end-use properties which are not met by corn grain of standard composition. Most commonly, such "specialty" corn is differentiated from "normal" field corn by altered endosperm properties, such as an overall change in the degree of starch branching (waxy corn, amylose extender; Glover, D. V. and E. T. Mertz, 1987, Corn, In: Nutritional Quality of Cereal Grains: Genetic and Agronomic Improvement, R. A. Olson and K. J. Frey, eds. American Society of Agronomy, Madison, Wis., pp. 183–336), increased accumulation of sugars or water-soluble polysaccharides (sugary, shrunken, supersweet corn; Glover, D. V. and E. T. Mertz, 1987, Corn, In: Nutritional Quality of Cereal Grains: Genetic and Agronomic Improvement, R. A. Olson and K. J. Frey, eds. American Society of Agronomy, Madison, Wisconsin, pp. 183–336) or alterations in the degree of endosperm hardness (food grade corn, popcorn; Glover, D. V. and E. T. Mertz, 1987, Corn. In: Nutritional Quality of Cereal Grains: Genetic and Agronomic Improvement, R. A. Olson and K. J. Frey, eds. American Society of Agronomy, Madison, Wisconsin, pp. 183–336; Rooney, L. W. and S. O. Serna-Saldivar, 1987, Food Uses of Whole Corn and Dry-Milled Fractions, In: Corn:Chemistry and Technology, S. A. Watson and P. E. Ramstead, eds. American Association of Cereal Chemists, Inc., St. Paul, Minn., pp. 399–429). Specialty corn types are typically grown under contract for production for specific end users who place value on starch quality or other specific kernel quality attributes. Perhaps outstanding example of this differentiation is the contract production of waxy maize, whereby inclusion of a single homozygous recessive gene (wx) converts normal maize snatch (75–80% amylopectin, 20–25% amylose) nearly completely to amylopectin (>99%). In a similar fashion the recessive gene amylose extender (ae) when homozygous, or the dominant gene Ae-5180 when homozygous or heterozygous (Plant Biotechnology, February 1991, Office of Biotechnology, Iowa State University, Ames, Iowa) increases the specific amylose content of the corn grain to 50% or greater. Additionally, U.S. Pat No. 4,798,735 teaches how modified corn starches produced by combinations of simple recessive genes can result in the production of starch with functional properties optimally suited for use in the foods industry. Sweet corn is yet another example of a specialty corn product often grown under contract, where the inclusion of the recessive genes sugary, shrunken-2 or sugary enhancer, singly or in combination, confers sweetness through a reduction in the amount of starch and an increase in the amount of glucose, sucrose, and/or water soluble polysaccharides normally found in the immature corn kernel (Creech, R. and D. E. Alexander, 1978, Breeding for Industrial and Nutritional Quality in Maize, In: Maize Breeding and Genetics, D. B. Walden, ed. John Wiley and Sons, New York, pp. 249–264).

More recently, there is a trend to differentiate corn not only on the basis of alterations in carbohydrate quality but also on the basis of its protein, oil, and kernel hardness characteristics. Several companies market corn with increased lysine (Crow's Hybrid Corn Company, Milford, Ill.), protein (Wilson Hybrids, Harlan, Iowa) oil (Pfister Hybrid Corn Company, El Paso, Illinois under the trademark KERNOIL®) and endosperm hardness (Vineyard Seed Co., Homer, Ill.) in an effort to serve markets placing increasing value on these grain attributes. Protein and oil content are particularly important determinants of the performance of corn as a component of animal feed (Glover, D. V. and E. T. Mertz, 1987, Corn, In: Nutritional Quality of Cereal Grains: Genetic and Agronomic Improvement, R. A. Olson and K. J. Frey, eds. American Society of Agronomy, Madison, Wis., pp. 183–336; Hat, Y., C. M. Parsons, and D. E. Alexander, 1987, Nutritive Value of High Oil Corn for Poultry. Poultry Science 66:103–111). Furthermore, as coproducts of wet and dry milling, corn oil and protein are important sources of revenue to wet and dry millers. Recent Iowa State University corn performance trials provide a means for recognizing the industrial value of these corn constituents by reporting not only the yield of tested hybrids but also their calculated wet milling and feed values. (Iowa Corn Growers Association, 1989, Higher Processing Value in 1989 State Fair Open Class Corn and Soybeans. Bulletin, Aug. 27, 1989)

The breeding, development, and nutritional attributes of high oil corn are described below as illustrative of the state of development, heritability, breeding difficulty, and economic advantage attendant to the development of many if not all enhanced quality grain traits. Perhaps the most thoroughly studied high-oil corn populations are the Illinois High Oil (IHO) and Alexander High Oil (Alexho) populations developed at the University of Illinois. IHO was developed by modified mass selection within the open pollinated corn variety, Burr's White, over more than 80 cycles of selection commencing in 1896 (Alexander, D. E., 1988, High Oil Corn: Breeding and Nutritional Properties, In: Proceedings of the 43rd Annual Corn and Sorghum Industrial Research Conference, pp. 97–105; Dudley, J. W., R. J. Lambert, and D. E. Alexander, 1974, Seventy Generations of Selection for Oil and Protein Concentration in the Maize Kernel, In: Seventy Generations of Selection for Oil and Protein in Maize, J. W. Dudley, ed. Crop Science Society of America, Madison, Wis., pp. 181–212). The highest average kernel or grain oil content achieved in this population is about 22% oil on a dry weight basis. In contrast, Dr. Denton Alexander, employing both mass and single kernel selection within a synthetic population (Alexho), was able to achieve an average oil content of approximately 22% following 28 cycles of selection (Alexander, D. E., 1988, High Oil Corn: Breeding and Nutritional Properties, In: Proceedings of the 43rd Annual Corn and Sorghum Industrial Research Conference, pp. 97–105). A number of corn inbreds have been released from the IHO (R802A) and Alexho (R805, R806) populations and are available to the public through the Director of Agricultural Experiment Station, University of Illinois, Urbana, Ill.

Oil content in corn is a grain quality attribute that is quantitatively inherited (Silvela, L., R. Rodgers, A. Garrera and D. E. Alexander, 1989, Effect of Selection Intensity and Population Size on Percent Oil in Maize, *Zea mays* L. Theoretical and Applied Genetics 78:298–304). Several studies indicate that oil content of bulked F2 kernels arising from crosses between various Alexho derivatives and inbred lines of normal oil content approaches the midparent value of oil content of kernels arising from the self-pollination of each parent separately (Alexander, D. E., 1988, High Oil Corn: Breeding and Nutritional Properties, In: Proceedings of the 43rd Annual Corn and Sorghum Industrial Research Conference, pp. 97–105; Misevic, D., A. Marie, D. E. Alexander, J. Dumanovic, and S. Ratkovic, 1989, Population Cross Diallele Among High Oil Populations of Maize. Crop Sci., 29:613–617). Additionally, F2 grain arising from high-oil X low-oil crosses has been observed to segregate for oil content on an individual kernel basis (Alexander, D. E., 1988, High Oil Corn: Breeding and Nutritional Properties, In: Proceedings of the 43rd Annual Corn and Sorghum Industrial Research Conference, pp. 97–105). Both of these characteristics are consistent with the hypothesis that oil content in corn seed or grain is controlled by the action of several genes, each of which makes a partial contribution to the overall oil content.

Because the genetic heterogeneity is kept high during the initial phases of most recurrent selection programs, it takes substantially longer to develop an agronomically elite inbred from a recurrent selection program than from a program based on pedigree breeding. To date, the majority of high-oil corn exists as populations exhibiting varying degrees of genetic nonuniformity. Despite efforts over the last thirty years to develop commercial high oil corn varieties by a combination of recurrent selection and pedigree breeding methods only a small number of commercially successful high oil inbreds have been produced, and only a limited number of high oil hybrid varieties have been grown on a commercial scale.

The widespread production of high-oil corn to meet the needs of poultry producers, swine feeders, and the corn milling industry is substantially delayed now because of limitations of current breeding procedures. Widespread production would be greatly enhanced if new methods of inbred development were found or if new hybrid production practices were available.

SUMMARY OF THE INVENTION

The present invention teaches a novel method for the production corn grain containing enhanced quality grain traits by commercial growers. The method results in the production of grain with enhanced quality traits following the pollination of a high-yielding plant by plants containing genes for enhanced quality grain traits. The plants enhanced in a quality grain trait employed as pollinators need not be genetically homozygous (inbred) or even homogeneous in appearance and need not be selected for combining ability with high-yielding female plants. In this way the breeding timeline for the production of commercially successful enhanced quality grain trait parents is significantly and dramatically reduced, and the commercial production of grain with enhanced quality traits is greatly accelerated. This method will catalyze a great expansion in the number of available agronomically elite female plants that can be used for the production of grain incorporating enhanced quality traits, thus increasing the yield and production range corn varieties expressing enhanced quality grain traits.

Specifically, Applicants have developed a method of enhancing a quality grain trait in corn grain comprising the steps of:

(a) planting in close proximity:
   (1) corn seed of a high-yielding variety to obtain female corn plants; and
   (2) corn seed of a variety, enhanced in a quality grain trait, which variety is nonisogenic to said female corn plants to produce corn plants enhanced in said quality grain trait capable of serving as pollinators;

(b) permitting said corn plants enhanced in said quality grain trait to pollinate said female corn plants;

(c) harvesting the resulting corn grain on all corn plants, thereby obtaining a high yield of corn grain enhanced in said quality grain trait intermediate in value between that found in kernels obtained following self-pollination of said quality grain trait and said female corn plants.

DETAILED DESCRIPTION OF THE INVENTION

For purposes of this application, we define the following terms:

Corn. Any variety, cultivar or population of *Zea mays* L.

Elite. This term characterizes a plant or variety possessing favorable traits, such as, but not limited to, high yield, good grain quality, and disease resistance. This enables its use in commercial production of seed or grain at a profit. The term also characterizes parents giving rise to such plants or varieties.

"This is a Quality Grain Trait found in the kernels arising from crosses between a female corn line and pollinator corn plants which is different in quantity from that found in the female corn line itself. Enhancement may involve either an increase in a property or characteristic deemed advantageous resulting in a higher amount or level of the Quality Grain Trait, or a decrease in a property or characteristic deemed detrimental resulting in a lower amount or level of the Quality Grain Trait."

Female corn plant. A corn plant that is incapable of producing any/or releasing functional pollen.

Field corn. These are varieties or cultivars of corn grown extensively on large acreages within a broad but defined geographic area for the production of grain and/or forage. Most field corn in the United States is also referred to as "dent" corn, whereas field corn produced in Europe and Argentina is more likely to be referred to as "flint" or "flint-dent" corn.

General Combining Ability. This is the average or overall performance of a genetic strain in a series of crosses.

Germ. This is the embryo of the corn kernel and contains the vast majority of the oil found in the kernel.

Grain. This comprises mature corn kernels produced by commercial growers for on-farm use or for sale to customers, in both cases for purposes other than growing or reproducing the species. Typical customers would include livestock feeders, wet or dry millers, or animal feed formulators.

Heterozygous. A genetic condition existing when different alleles reside at corresponding loci on homologous chromosomes.

High-Amylose Corn (Kernel). A kernel which contains starch comprising elevated levels of amylose when compared to a low amylose corn kernel.

High-Amylose Corn (Plant). This is a plant which, when self pollinated, will give rise to kernels containing starch comprising elevated levels of amylose when compared to a low amylose corn plant.

High-Oil Corn (Kernel). A kernel which contains elevated levels of oil on a percent dry weight basis when compared to low-oil corn kernels.

High-Oil Corn (Plant). This is a plant which, when self pollinated, will give rise to kernels containing elevated levels of oil on a percent dry weight basis when compared to a low-oil corn plant.

High-Oleic Corn (Plant). This is a plant which, when self pollinated, will give rise to kernels containing an oil comprising a higher weight percentage of oleic acid among total fatty acids that is found in a low-oleic acid corn plant.

Homozygous. A genetic condition existing when identical alleles reside at corresponding loci on homologous chromosomes.

Hybrid. Any offspring of a cross between two genetically unlike individuals (Rieger R., A. Michaelis and M. M. Green, 1968, A Glossary of Genetics and Cytogenetics, Springer-Verlag, N.Y.)

Inbred. A substantially homozygous individual or variety.

Kernel. This is the corn caryopsis, comprising in part a mature embryo and endosperm which are products of double fertilization. Also, the corn fruit.

Low-Amylose Corn (Kernel). This is a kernel which contains starch comprising approximately 20–25 percent amylose on a weight basis.

Low-Amylose Corn (Plant). This is a plant which, when self pollinated, will give rise to kernels which contain starch comprising approximately 20–25 percent amylose on a weight basis.

Low-Oil Corn (Kernel). A kernels which contains oil in the range of about 2.5–5.1 percent on a dry weight basis.

Low-Oil Corn (Plant). This is a plant which, when self pollinated, will give rise to kernels containing levels of oil in the range of about 2.5–5.1 percent on a dry weight basis. This level of oil is typical of a wide range of field corn inbreds and hybrids.

Low-Oleic Corn (Plant). This is a plant which, when self pollinated, will give rise to kernels containing an oil in which oleic acid comprises 30 percent or less of the total fatty acids by weight.

Maize. This is any variety, cultivar, or population of Zea mays L.

Male Sterile. This is a plant(s) which fails to produce functional pollen as a consequence of mechanical or hand de tasseling, incorporation of genetic sterility, or by other mechanisms.

Nonisogenic. A state of genetic dissimilarity between individuals, inbreds, hybrids, or varieties obtained when their nuclear genetic compliments possess less than statistical similarity. Nonisogenicity can be reduced, for example, by backcrossing a variety at least 3 times to a recurrent patent which is itself genetically homogeneous or inbred.

Ovule. This is a structure consisting of female reproductive tissue surrounded by maternal tissue. During the development of a corn plant the ovule will eventually contain a haploid egg nucleus and two haploid polar nuclei. Following fusion with sperm nuclei found in pollen, the ovule will develop into a mature corn kernel.

Percent (%) Amylose. This is the concentration of amylose found in the starch extracted from corn kernels expressed on a dry weight basis.

Percent (%) Lysine. This is the concentration of lysine found in a corn kernel expressed on a dry weight basis.

Percent (%) Oleic (Acid). This is the concentration of oleic acid expressed on a weight basis found in the oil extracted from corn kernels.

Percent (%) Oil. This is the oil concentration of a corn kernel expressed on a dry weight basis.

Percent (%) Protein. This is the total protein concentration of a corn kernel expressed on a dry weight basis.

Pollen. In corn, this is a structure which ultimately contains the two haploid sperm nuclei which fuse with the egg nucleus and polar nuclei found in the ovule to give rise to the embryo and endosperm of the mature corn kernel.

Population. This is a genetically heterogeneous collection of plants sharing a common genetic derivation.

Quality Grain Trait. Such traits relate to the intermediate or final use of grain and include but are not limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility of grain to breakage and spoilage, among others.

Seed. This is the mature corn kernel produced for the purpose of propagating the species. Alternately, it is a corn kernel commonly sold to commercial grain producers or growers.

Specific Combining Ability. This is the performance of specific combinations of genetic strains in crosses in relation to the average performance of all combinations.

Synthetic (Population). This is a genetically heterogeneous collection of planes of known ancestry created by the intermating of any combination of inbreds, hybrids, varieties, populations, races, or other synthetics.

Variety or cultivar. This is a group of similar plants that by structural features and performance can be identified from other varieties within the same species.

The corn kernel is a product of double fertilization (Kiesselbach, T. A., 1980, The Structure and Reproduction of Corn, University of Nebraska Press). This means that both the diploid embryo (giving rise the germ and seedling) and the triploid endosperm (the nutritive structure surrounding the germ) contain genes transmitted from both the male and female parents. Nonetheless, the genes affecting grain composition and quality are similar enough in most field corn inbreds that crossing any given female with a large variety male plants does not result in dramatic changes in the compositional or quality characteristics of the resulting seed or grain. Likewise, planting different field corn hybrids within pollinating proximity to each other will not, in most cases, substantially affect the quality of the grain harvested on each type.

In contrast, a minority of commercial corn inbreds or hybrids do contain genes which substantially modify grain quality. These hybrids, such as those containing the waxy gene, must be isolated from normal, non-waxy corn inbreds or hybrids in order to recover waxy seed or grain. If a non-waxy pollen grain (as found in most field corn inbreds and hybrids) pollinates an ovule borne on a waxy inbred or hybrid, the resulting kernel will be non-waxy, even though adjacent kernels on the same ear, pollinated by waxy pollen, will remain waxy. This immediate effect of pollen genotype on kernel characteristics is termed "xenia". (Rieger, R., A. Michaelis and M. M. Green, 1968, A Glossary of Genetics and Cytogenetics, Springer-Verlag, New York) and the hybrid nature of such kernels is recognizable by particular phenotypic characteristics (color, shape, size, etc.) owing to the direct influence exerted by the genotype of the pollen.

This immediate effect of pollen genotype on grain quality has been observed with pollen obtained from high-oil corn plants (Alexander, D. E. and R. J. Lambert, 1968, Relationship of Kernel Oil Content to Yield in Maize Crop Science 8:272–274). In addition, xenia can be observed for several other quality grain traits including but not limited to protein quantity, protein quality, oil quality, starch quality, kernel pigmentation and kernel hardness. We may well be able to observe xenia for several other quality grain traits not specifically listed. We have expanded this observation to develop it into a useful method for producing corn grain with enhanced grain quality traits.

The present invention is further defined in following Examples, in which all parts and percentages are by dry weight basis and temperatures are given in degrees Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Demonstration that kernels arising on low-oil corn inbreds pollinated by high-oil male corn plants are themselves high in oil Low-oil inbreds and high-oil pollinators were grown at the DuPont Company Stine-Haskell Research Center in Newark, Delaware, during the summer of 1989. Low-oil plants used as female were either homozygous for the recessive genes waxy (wx), opaque-2 (o2), or carried the normal alleles an these loci (no designation). Silks arising on ears from these plants were dusted by hand with fresh pollen from high-oil plants which were either high-oil corn inbreds (AEC27-2S6), partially inbred high-oil corn lines (UHOC3-41 S3; UHOC3-131 S3; UHOC3-168 S3), individuals from a high-oil synthetic population (ASKC28), or individuals from a high-oil corn variety (IHO). Pollination involved bagging immature ears to prevent contamination by stray pollen and collection of fresh pollen in tassel bags as is well known in the breeder's art. Hybrid kernels arising on these ears were harvested by ear at maturity and dried. Bulk kernels on each ear were subjected to intact kernel oil quantity analysis by near infrared transmission spectrophotometry. (Williams, P. C., 1987, Commercial Near Infrared Reflectance Instrumentation, In: Near Infrared Technology in the Agricultural and Food Industries; Williams, P. C. and C. Norris, eds. American Association of Cereal Chemists). Oil values were corrected for moisture and are expressed as a percentage on a kernel dry weight basis. Midparent values were calculated as the average of the oil values found in self-pollinated grain arising on sib male and sib female plants.

TABLE 1

| FEMALE | | POLLINATOR | | HYBRID KERNELS | | |
|---|---|---|---|---|---|---|
| Source | Percent Oil | Source | Percent Oil | Percent Oil | Midparent | Percent Increases§ |
| Mo17 | 3.19 | AEC27-2 S6 | 7 | 3.9 | 5.1 | 22 |
|  |  | UHOC3-131 S3 | 10.5 | 5.6 | 6.9 | 76 |
|  |  | UHOC3-168 S3 | 12.8 | 5 | 8 | 57 |
|  |  | ASKC28 | 20.6 | 6.7 | 11.9 | 110 |
|  |  | IHO | 15.8 | 5.3 | 9.5 | 66 |
| LH51 | 3.34 | UHOC3-168 S3 | 12.8 | 5.7 | 8.1 | 71 |
|  |  | ASKC28 | 20.6 | 7.3 | 12 | 119 |
| B73 | 3.9 | AEC27-2 S6 | 7 | 4.8 | 5.6 | 23 |
|  |  | UHOC3-41 S3 | 11.9 | 6.1 | 8.1 | 56 |
|  |  | UHOC3-168 S3 | 12.8 | 5.9 | 8.5 | 51 |
|  |  | ASKC28 | 20.6 | 10 | 12.4 | 156 |
|  |  | IHO | 15.8 | 4.5 | 10 | 15 |
| Mo17 wx | 3.87 | AEC27-2 S6 | 7 | 4.3 | 5.4 | 11 |
|  |  | UHOC3-41 S3 | 11.9 | 5.8 | 7.9 | 50 |
|  |  | ASKC28 | 20.6 | 8.4 | 12.2 | 117 |
| LH51 wx | 3.78 | AEC27-2 S6 | 7 | 4.6 | 5.4 | 22 |
|  |  | UHOC3-41 S3 | 11.9 | 6.4 | 7.9 | 69 |
|  |  | ASKC28 | 20.6 | 8.7 | 12.2 | 130 |
|  |  | IHO | 15.8 | 6.3 | 9.8 | 67 |
| B73 HT wx | 3.9* | AEC27-2 S6 | 7 | 5.2 | 5.5 | 33 |
|  |  | UHOC3-41 S3 | 11.9 | 6.3 | 8 | 62 |
|  |  | ASKC28 | 20.6 | 10.8 | 12.2 | 177 |
|  |  | IHO | 15.8 | 5.6 | 9.9 | 44 |
| B37 wx | 3.2 | AEC27-2 S6 | 7 | 5.1 | 5.1 | 59 |
|  |  | UHOC3-131 S3 | 10.5 | 5.4 | 6.8 | 61 |
|  |  | UHOC3-168 S3 | 12.8 | 6.9 | 8 | 116 |
|  |  | ASKC28 | 20.6 | 7.2 | 11.9 | 125 |
|  |  | IHO | 15.8 | 6.2 | 9.5 | 94 |
| Oh43 wx | 2.6 | AEC27-2 S6 | 7 | 4.8 | 4.8 | 85 |

TABLE 1-continued

| FEMALE | | POLLINATOR | | HYBRID KERNELS | | |
|---|---|---|---|---|---|---|
| Source | Percent Oil | Source | Percent Oil | Percent Oil | Midparent | Percent Increases§ |
| | | UHOC3-131 S3 | 10.5 | 5.4 | 6.5 | 108 |
| | | UHOC3-168 S3 | 12.8 | 5.8 | 7.7 | 123 |
| | | ASKC28 | 20.6 | 8.9 | 11.6 | 242 |
| | | IHO | 15.8 | 5.7 | 9.2 | 119 |
| A632 wx | 3.9 | AEC27-2 S6 | 7 | 5.1 | 5.4 | 31 |
| | | UHOC3-131 S3 | 10.5 | 5.8 | 7.2 | 49 |
| | | ASKC28 | 20.6 | 8.9 | 12.2 | 128 |
| | | IHO | 15.8 | 8.2 | 9 | 110 |
| LH74 wx | 4.1 | UHOC3-41 S3 | 11.9 | 7 | 8 | 71 |
| | | ASKC28 | 20.6 | 9.8 | 12.3 | 139 |
| | | IHO | 15.8 | 5.7 | 10 | 39 |
| LH82 wx | 4.14 | AEC27-2 S6 | 7 | 6 | 5.6 | 45 |
| | | UHOC3-41 S3 | 11.9 | 6.9 | 8.1 | 67 |
| | | ASKC28 | 20.6 | 11.5 | 12.4 | 178 |
| | | IHO | 15.8 | 4.8 | 10 | 16 |
| Mo17 o2 | 3.5* | AEC27-2 S6 | 7 | 4.9 | 5.2 | 40 |
| | | UHOC3-41 S3 | 11.9 | 6.2 | 7.7 | 77 |
| | | UHOC3-168 S3 | 12.8 | 5.7 | 8.1 | 63 |
| | | ASKC28 | 20.6 | 8.7 | 12 | 149 |
| | | IHO | 15.8 | 5.4 | 9.7 | 54 |

* = Oil Content of Parent Seed to Female
§ = Percent Increase in Oil Concentration over Female As shown in Table 1, kernels arising from crosses between a number of low-oil inbred corn lines and high-oil corn plants always contain levels of oil which are significantly higher than seen in the low-oil inbreds themselves.

In most cases the oil concentration in the hybrid kernels increases as the concentration of oil in the high-oil corn variety serving as a pollinator increases. This increase in oil concentration in hybrid kernels is dramatic when compared to the oil concentration low-oil source inbred in all cases where a high-oil source variety is used as pollinator. This is true whether the high-oil corn plants serving as pollinator are inbreds, members within a partially inbred line, members of a synthetic population, or comprise a high-oil variety. The increase in the oil content of hybrid grain is especially evident when ASKC28 is used as pollinator, in which case increases in oil content in excess of 100 percent over the low-oil parent are routinely seen; in one case an increase of well over 200 percent was observed.

Hybrid kernels arising from pollinations involving IHO appear to be anomalously low in oil content as evidenced by their low percent midparent values. This may be due to the fact that IHO is genealogically distinct from the other high-oil pollinators, and hence may contain genes which behave differently from the other high-oil pollinators employed in this Example.

The inbreds LH51, B73, LH51 wx, B73 HT wx, LH74 wx, and LH82 wx are available commercially from Holden Foundation Seed Company, Williamsburg, Iowa. Those denominated Mo17, Mo17 wx, B73 wx, Oh43 wx, A632 wx, and Mo17 o2 are available from the Maize Genetics Coop, University of Illinois Agronomy Department, University of Illinois, Urbana, Ill.

EXAMPLE 2

Demonstration that kernels arising on low-oil corn hybrids pollinated by high-oil corn inbreds, and kernels arising on high-oil corn hybrids pollinated by either low-oil or high-oil corn inbreds, are themselves high in oil Low-oil or high-oil inbreds and hybrids were grown at El Paso, Illinois during the Summer of 1989. Several low-oil [Pioneer 3377, Pioneer 3379, Pfister 2995 and high-oil [X124, KERNOIL®-4, X122, X326, and X327] corn hybrids were used as female and were pollinated by hand with pollen arising on either a low-oil (LH123) or a high-oil (LP11) inbred. Hand pollinations were accomplished following procedures well known to the breeder's art. Hybrid kernels arising on these ears were harvested by ear at maturity and dried. Hulk kernels from each ear which were subjected to oil analysis were dried to less than 8% moisture. The oil content of intact kernels was determined by wide-line nuclear magnetic resonance spectroscopy (Alexander, D. Z., L. Silvela, F. I. Collins, and R. C. Rodgers, 1967, Analysis of Oil Content of Maize by Wide Line NMR, J. Am. Oil Chem. Soc., 44:555–558), and oil concentration expressed on a dry weight percent basis.

TABLE 2

| FEMALE | | POLLINATOR | | HYBRID KERNELS | | |
|---|---|---|---|---|---|---|
| Source | Percent Oil | Source | Percent Oil | Percent Oil | Mid-parent | Percent Increase§ |
| Pioneer 3379 | 4.8 | LP11 | 9.0 | 7.0 | 6.9 | 46 |
| | | LH123 | 4.4 | 4.7 | 4.6 | 0 |
| Pfister 2995 | 4.9 | LP11 | 9.0 | 7.0 | 6.9 | 43 |
| | | LH123 | 4.4 | 4.7 | 4.6 | 0 |
| Pioneer 3377 | 5.1 | LP11 | 9.0 | 7.1 | 7.0 | 39 |
| | | LH123 | 4.4 | 4.9 | 4.7 | 0 |
| X124 | 6.5 | LP11 | 9.0 | 8.1 | 7.7 | 25 |
| | | LH123 | 4.4 | 5.4 | 5.4 | (−17) |
| KERNOIL ®-4 | 7.5 | LP11 | 9.0 | 8.5 | 8.3 | 13 |
| | | LH123 | 4.4 | 6.1 | 6.0 | (−19) |
| KERNOIL ®-8 | 7.5 | LP11 | 9.0 | 8.0 | 8.3 | 7 |
| | | LH123 | 4.4 | 6.2 | 6.0 | (−17) |
| X326 | 7.5 | LP11 | 9.0 | 8.4 | 8.2 | 12 |
| | | LH123 | 4.4 | 6.0 | 5.9 | (−20) |
| X327 | 7.6 | LP11 | 9.0 | 8.3 | 8.3 | 9 |
| | | LH123 | 4.4 | 6.0 | 6.0 | (−22) |

§ = Percent Increase in Oil Concentration over Female. Negative increases in parentheses are decreases.

The data in Table 2 demonstrate that the xenia effect for oil content was not confined to crosses using only inbred lines as female. The oil content of hybrid kernels arising from crosses among either high-oil or low-oil hybrids (used as female) and high-oil inbred varieties serving as pollinators are themselves high in oil. Similarly, kernels arising from crosses between a high-oil hybrid female and a low-oil inbred male is also high in oil, although in this case the oil content of the hybrid kernels was lower than that of the high-oil female parent. Crosses among low-oil hybrids and low-oil inbreds gave rise to grain low in oil content.

In all of the combinations involving at least one high-oil parent the oil content of the kernels harvested on the female plants approach the midparent value. Thus, if a high-oil hybrid female is employed as a parent in a cross, the resulting hybrid kernels arising following pollination by an inbred plant are also high in oil.

Pioneer 3377 and 3379 are commercially available from Pioneer Hybrids, Johnston City, Iowa. Pfister 2995, Kernoil®-4 and Kernoil®-8 are commercially available from Pfister Hybrids, El Paso, Ill.

EXAMPLE 3

Demonstration that kernels arising on low-oil hybrids pollinated by hybrids of increased oil content demonstrate a significant increase in oil Kernels from the low-oil hybrid Pfister 3450 and several hybrids [X121, X325, X326, X327, X338, and X354] high in oil when grown in the central corn growing regions of the United States were sown in a field near Rosario, Argentina in October 1989 and grown during the ensuing season. Hand pollinations among these varieties were performed by procedures well known to the breeders art. Hybrid kernels arising on these ears were harvested by ear at maturity and dried. Bulk kernels on each ear were subjected to intact kernel oil quantity analysis by near infrared transmission spectrophotometry. Oil values were corrected for moisture and are expressed on a kernel dry weight percentage basis. Midparent values were calculated as the average of the oil values found in self-pollinated grain arising on sib male and sib female plants.

TABLE 3

| FEMALE | | POLLINATOR | | HYBRID KERNELS | | |
|---|---|---|---|---|---|---|
| Source | Percent Oil | Source | Percent Oil | Percent Oil | Mid-parent | Percent Increase§ |
| Pfister 3450 | 2.94 | X325 | 4.61 | 4.45 | 3.78 | 56 |
| | | X338 | 4.73 | 4.21 | 3.84 | 43 |
| | | X326 | 4.74 | 4.65 | 3.84 | 58 |
| | | X327 | 4.75 | 4.4 | 3.84 | 50 |
| | | X354 | 5.46 | 4.08 | 4.2 | 39 |
| | | X121 | 5.62 | 4.13 | 4.28 | 40 |

§ = Percent Increase in Oil Concentration over Female

As shown in Table 3, several of the hybrids known to express high-oil when grown in the United States corn belt did not do so in this rest in Argentina (X325, X338, X326, X327), although X354 and X121 did classify as high-oil hybrids in this test. Nonetheless, even in this environment, the oil content of the hybrids employed as pollinators was substantially higher than the oil content of the hybrid variety employed as female. Hybrid kernels recovered from these crosses again exhibited oil contents at or above their midparent values. This demonstrates that a xenia effect for oil quantity is apparent when a hybrid of low-oil content is pollinated by a variety of hybrids containing levels of oil substantially above that of the hybrid employed as female.

Pfister 3450 is commercially available from the Pfister Hybrids, El Paso, Ill.

EXAMPLE 4

Demonstration that kernels arising on a low-oil corn hybrid open pollinated by plants comprising a high-oil corn synthetic population are themselves high in oil A large research experiment was conducted in Humboldt, Iowa during the summer of 1990 to examine the yield and quality of kernels arising on ears borne on male-sterile hybrid following pollination by the high-oil pollinator ASKC28. The experimental treatments consisted of blocks containing varying populations of the low-oil male sterile hybrid Pfister 3000 ms interplanted with a constant population of the male-fertile high-oil synthetic population ASKC28. To aid in distinguishing these two plant varieties during pollen shed and at harvest ASKC28 seed was planted a few inches to the side of each row containing Pfister 3000 ms. Check plots were planted with varying concentrations of the low-oil male fertile hybrid Pfister 3000 (a blend of 50% Pfister 3000 male fertile and Pfister 3000 male sterile (ms) plants) alone. Pfister 3000 and Pfister 3000 ms are isogenic, and are expected to behave similarly with respect to yield and kernel quality. The experiment was of randomized complete block design with four replications per treatment. To minimize the spread of pollen between blocks each block was surrounded by 100 feet of Pfister 3000 ms on all sides.

Kernels on all plants arose by open pollination. Because Pfister 3000 ms is male sterile and sheds little or no pollen, kernels arising on ears borne by either ASKC28 plants or Pfister 3000 ms plants are considered to have arisen following fertilization by ASKC28 pollen in the majority of cases. At maturity, several ears from each replication of each treatment were harvested separately, dried on the ear, shelled, and kernels within each replication of each treatment bulked. The total oil concentration of the shelled kernels was determined gravimetrically according to Method 920.39 of the Association of Official Analytical Chemists and is reported on a percent dry matter basis throughout this Example.

TABLE 4

| | Population Density§ | | |
|---|---|---|---|
| Source | Source | Total | Source Oil |
| Pfister 3000 | 14,000 | 14,000 | 4.60 |
| Pfister 3000 | 18,000 | 18,000 | 4.47 |
| Pfister 3000 | 22,000 | 22,000 | 4.33 |
| Pfister 3000 | 24,000 | 24,000 | 4.46 |
| ASKC28 | 8,000 | 24,000 (a)* | 20.02 |
| ASKC28 | 8,000 | 28,000 (b) | 18.20 |
| ASKC28 | 8,000 | 32,000 (c) | 18.28 |

§Plants/acre
*remaining 16,000 (a), 20,000 (b) or 24,000 plants were Pfister 3000 ms The oil content of kernels obtained from ears of the low-oil hybrid Pfister 3000 and the high-oil synthetic ASKC28 are listed in Table 4. Kernels arising on ASKC28 ears following open sib pollination by ASKC28 exhibited significantly higher levels of oil than did kernels arising on the hybrid Pfister 3000 (open pollinated with Pfister 3000 pollen) at all plant population densities tested.

TABLE 5

| FEMALE | | POLLINATOR | | HYBRID KERNELS | | |
| --- | --- | --- | --- | --- | --- | --- |
| Source | Population | Source | Population | Population | Percent Oil | Percent Increase§ |
| Pf 3000ms | 16,000 | ASKC28 | 8,000 | 24,000 | 11.10 | 149 |
| Pf 3000ms | 20,000 | ASKC28 | 8,000 | 28,000 | 11.18 | N/C* |
| Pf 3000ms | 24,000 | ASKC28 | 8,000 | 32,000 | 11.67 | N/C |

§ = Percent Increase in Oil Concentration over Female
* = Not Calculated

The oil content of kernels arising on Pfister 3000 ms plants pollinated by ASKC28 pollen is given in Table 5. At total plant population densities of 24,000, 28,000, and 32,000 plants-per-acre these kernels exhibited a significantly higher oil concentration than that found in kernels arising on open pollinated Pfister 3000 male fertile hybrid plants at similar or lower total planting densities. For example, at a total planting density of 24,000 plants/acre, the oil content of kernels borne on Pfister 3000 ms plants (pollinated by ASKC28) is 11.1 percent, a 149 percent increase over the oil content of open pollinated Pfister 3000 male fertile plants (4.46 percent). This density approximates that commonly employed by commercial growers across highly productive areas of the United States corn belt.

Finally, the maxim obtainable oil concentration in kernels arising on Pfister 3000 ms following pollination by ASKC28 may be higher than determined in this Example, since any pollen contamination due to incomplete sterility in Pfister 3000 ms would lead to a lowering of oil concentration in kernels harvested on Pfister 3000 ms plants.

Taken together, the data in Table 4 and Table 5 clearly show a xenia effect for oil content of hybrid kernels arising following pollination of the low-oil Pfister 3000 ms by ASKC28.

Pfister 3000 and Pfister 3000 ms are available commercially from Pfister Hybrids, El Paso, Ill.

EXAMPLE 5

Demonstration that kernels arising on corn inbreds low in oleic acid content crossed with corn inbreds high in oleic acid content are themselves high in oleic acid Corn inbreds or lines exhibiting either high or low concentrations of oleic acid in kernels obtained following self pollination were planted in Nov. 1990 or 1991 in Molokai, Hi. or in the summer of 1990 at the DuPont Company Stine-Haskell Research Center in Newark, Del. These lines were self, sib, or cross pollinated by hand following methods well known to the breeder's art as outlined in general form in Example 1. At maturity ears were hand harvested, dried, and shelled.

To determine the oleic acid content of oil in corn kernels, the oil was recovered from ground kernels by either hexane or chloroform extraction and treated with sodium methoxide. The resulting fatty acid methyl esters were separated by capillary gas chromatography. In this Example oleic acid content is expressed a a percentage of the total fatty acid content of the oil extract.

TABLE 6

| Location | Source | Percent Oleic | Source | Percent Oleic | Percent Oleic | Mid-parent | Percent Increase§ |
| --- | --- | --- | --- | --- | --- | --- | --- |
| Molokai | B73 | 27 | B73ol | 62 | 42 | 45 | 93 |
| Molokai | LH51 | 21 | Va35 | 38 | 30 | 30 | 100 |
| Molokai | B73 | 26 | LH24 | 38 | 35 | 32 | 109 |
| Molokai | B73 | 26 | Va35 | 38 | 38 | 32 | 119 |
| Newark | B73 | 27 | Va35 | 41 | 35 | 34 | 103 |

§ = Percent Increase in Oil Concentration over Female

As shown in Table 6, hybrid kernels arising from the pollination of the low-oleic inbreds B73 or LH51 by pollen obtained from the high-oleic inbreds Va35, LH24, and B73ol contained levels of oleic acid significantly higher than those obtained following self- or sib-pollination of the low-oleic inbred parents themselves.

These data demonstrate a clear xenia effect for percent oleic acid content of oil produced in hybrid kernels following the pollination of a low-oleic corn line by a high-oleic corn line.

Inbred Va35 is available to the public from the Agronomy Department, Virginia Tech University, Blacksburg, Va. Inbred B73 is widely available, particularly from Iowa State University, Agronomy Department, Ames, Iowa. Inbred LH24 is commercially available from Holdens Foundation Seeds, Williamsburg, Iowa.

EXAMPLE 6

Demonstration that kernels arising on a lower-protein corn hybrid open-pollinated by members of a higher-protein corn synthetic modulation are themselves higher Kernels produced on the high-oil synthetic ASKC28 and the low-oil hybrids Pfister 3000 and Pfister 3000 ms in the experiment described in Example 4 were analyzed for total protein concentration by a modification of the Kjeldhal procedure described in Method 988.05 of the Association of Official Analytical Chemists. Throughout this Example the protein content of corn kernels is reported on a percent dry weight basis.

TABLE 7

| | Population Density§ | | |
| --- | --- | --- | --- |
| Source | Source | Total | Source Protein |
| Pfister 3000 | 14,000 | 14,000 | 9.95 |
| Pfister 3000 | 18,000 | 18,000 | 9.09 |
| Pfister 3000 | 22,000 | 22,000 | 8.46 |
| Pfister 3000 | 24,000 | 24,000 | 8.84 |
| ASKC28 | 8,000 | 24,000 (a)* | 12.61 |
| ASKC28 | 8,000 | 28,000 (b) | 12.77 |
| ASKC28 | 8,000 | 32,000 (c) | 12.66 |

§Plants/acre
*remaining 16,000 (a), 20,000 (b) or 24,000 plants were Pfister 3000 ms The protein content of kernels arising on ears of the hybrid Pfister 3000 following open pollination and the protein content of kernels arising on ASKC28 following open pollination are given in Table 7. Kernels arising on open pollinated ASKC28 ears exhibited significantly higher levels of protein than did kernels arising on the hybrid Pfister 3000 when sib pollinated at all plant population densities tested.

TABLE 8

| Female | | Male | | | |
|---|---|---|---|---|---|
| Source | Population | Source | Population | Total Population | Total Protein Hybrid Kernels |
| Pf 3000ms | 16,000 | ASKC28 | 8,000 | 24,000 | 10.22 |
| Pf 3000ms | 20,000 | ASKC28 | 8,000 | 28,000 | 9.82 |
| Pf 3000ms | 24,000 | ASKC28 | 8,000 | 32,000 | 9.82 |

The protein content of kernels arising on Pfister 3000 ms plants pollinated by ASKC28 is given in Table 8. At total plant population densities of 24,000, 28,000, and 32,000 plants per acre these kernels exhibited a significantly higher protein concentration than found in kernels arising on open pollinated Pfister 3000 hybrid plants at similar total planting densities (Table 7). This difference is most clearly seen at a planting density of 24,000 plants/acre, where the protein content of kernels arising on Pfister 3000 ms plants (pollinated by ASKC28) is significantly higher (10.22 percent) than that borne on open pollinated pollinated Pfister 3000 plants (8.84 percent). This planting density approximates that commonly employed by commercial growers for many corn hybrids across highly productive areas of the United States corn belt.

The protein content of corn grain is sensitive many factors, including but not limited to population density and soil fertility. For example, Table 7 shows that the protein content of kernels arising on Pfister 3000 by open pollination generally increases with decreasing population density over the range tested. However, the protein content of kernels arising on Pfister 3000 by open pollination (9.95 percent) approach that of kernels arising on Pfister 3000 ms pollinated by ASKC28 only at the lowest population density tested, 14,000 plants/acre. This is significantly lower than the planting density commonly employed by commercial growers for many corn hybrids across highly productive areas of the United States corn belt. It is likely the protein content of kernels arising on Pfister 3000 ms following pollination by ASKC28 would be higher than 9.95 percent under conditions where the two varieties were interplanted to a total population density of 14,000 plants/acre.

Finally, the maximum obtainable protein concentration in kernels arising on Pfister 3000 ms following pollination by ASKC28 may be higher than determined in this Example, since any pollen contamination due to incomplete sterility in Pfister 3000 ms would lead to a lowering of protein concentration in kernels harvested on Pfister 3000 ms plants.

Taken together the data presented in Table 7 and Table 8 clearly support a xenia effect for protein content in hybrid kernels which arise following pollination of Pfister 3000 ms by pollen produced by ASKC28.

Pfister 3000 and Pfister 3000 ms are commercially available from Pfister Hybrids, El Paso, Ill.

EXAMPLE 7

Demonstration that kernels arising on a lower-lysine corn hybrid open-pollinated by members of a higher-lysine corn synthetic population are themselves higher in lysine The low-oil hybrids Pfister 3000 and Pfister 3000 ms and the high-oil synthetic population ASKC28 were grown in the experimental plot in Humboldt, Iowa in 1990 previously described in Example 4. A research plot of similar design was also grown in Oran, Mo. during the summer of 1990. The hybrid [LH119 X ASKC28] was used as an additional pollinator in this experiment. At both locations kernels arising on Pfister 3000, Pfister 3000 ms, ASKC28, and [LH119 X ASKC28] were open pollinated, harvested, and bulked according to procedures described in Example 4.

The lysine concentration of kernels was determined by separating the amino acids obtained following acid digestion of defatted meal by high performance liquid chromatography. The individual amino acids were resolved by post column derivitization with ninhydrin. In this Example lysine content of kernels is expressed on a percent dry weight basis. The lysine content of kernels arising on Pfister 3000 and ASKC28 was determined following open pollination of each variety in isolation. The lysine content of hybrid kernels refers to that realized following open pollination of Pfister 3000 ms by pollen arising on ASKC28 or [LH119 ×ASKC28] plants.

TABLE 9

| Oran, Missouri | | | | | |
|---|---|---|---|---|---|
| Female | | Male | | Hybrid Kernels | |
| Source | Percent Lysine | Source | Percent Lysine | Percent Lysine | Percent Increase§ |
| Pfister 3000 | 0.194 | ASKC28 | 0.338 | 0.322 | 66 |
| Pfister 3000 | 0.194 | [LH119 X ASKC28] | 0.288 | 0.266 | 37 |
| Pfister 3000 | 0.194 | X354 | 0.280 | 0.262 | 35 |

§ = Percent Increase in Oil Concentration over Female

TABLE 10

| Humboldt, Iowa | | | | | |
|---|---|---|---|---|---|
| Female | | Male | | Hybrid Kernels | |
| Source | Percent Lysine | Source | Percent Lysine | Percent Lysine | Percent Increase§ |
| Pfister 3000 | 0.234 | ASKC28 | 0.335 | 0.340 | 45 |
| Pfister 3000 | 0.234 | [LH119 X ASKC28] | 0.351 | 0.388 | 50 |
| Pfister 3000 | 0.234 | X354 | 0.297 | 0.288 | 23 |

§ = Percent Increase in Oil Concentration over Female

Tables 9 and 10 show that kernels obtained from Pfister 3000 following open pollination contain from 0.194 to 0.235 percent lysine, which is typical of the lysine contents of most corn hybrids grown across the United States corn belt. In contrast, ASKC28 and [LH119 X ASKC28] both contain substantially higher levels of lysine than does Pfister 3000. Hybrid kernels arising on Pfister 3000 ms following pollination by either ASKC28 or [LH119 ×ASKC28] pollen also contain significantly higher lysine content than kernels arising on Pfister 3000 by open pollination. Taken together, the data in Table 9 and Table 10 clearly support a xenia effect for lysine concentration.

Pfister 3000 and Pfister 3000 ms are commercially available from Pfister Hybrids, El Paso, Ill.

EXAMPLE 8

Demonstration that kernels arising on a low-amylose corn variety pollinated by a high-amylose variety will themselves be high in amylose Corn kernels typically contain starch which is comprised of approximately 75 to 80 percent amylopectin and approximately 20 to 25 percent amylose. Many genes are currently known to affect either the starch content of corn kernels, the composition of that starch, or both. To illustrate, Ae-5180 is a corn gone which causes corn plants containing this gone to produce starch with an amylose content as high as 72%. Since this high amylose content is seen even in the case where the high amylose plant contains only one copy of Ae-5180 (Plant Biotechnology, Feb. 1991, Office of Biotechnology, Iowa State University, Ames, Iowa), pollen from plants containing Ae-5180 will exhibit xenia for percent amylose content realized in corn kernels arising on female corn plants.

Female corn plants, be they inbreds, hybrids, members of synthetic or natural populations, or any other corn varieties will be pollinated by high-amylose male corn plants which again may be inbreds, hybrids, members of synthetic or natural populations, or any other corn variety. Resulting hybrid kernels arising on the female corn plants will contain starch exhibiting elevated levels of amylose as compared to that obtained on female corn plants following self or sib pollination. The level of amylose in the hybrid kernels will approach or exceed the expected midparent amylose content as a percentage of total starch in the hybrid kernels. The preferred pollinator in this case would contain the gene Ae-5180, but other genes may be found which exhibit xenia for amylose content.

EXAMPLE 9

Demonstration that kernels arising on female corn plants pollinated by corn plants possessing genes for pigment content as an enhanced grain quality trait will themselves express enhanced grain quality traits for kernel pigmentation The corn kernel may contain several types of pigment, including but not limited to carotenoids, xanthophylls, and anthocyanins. Some of these pigments are of value in the chain of commerce, particularly the carotenoids and xanthophylls which are of value in the poultry industry, although other potential uses exist for these pigments. In other cases a reduction in certain pigments is desired. The genetics of pigment accumulation in corn kernels are complex but well known, and it is expected that the accumulation of kernel pigment will exhibit xenia.

Female corn plants, by they inbreds, hybrids, members of synthetic or natural populations or any other corn varieties will be pollinated by male corn plants which again may be inbreds, hybrids, members of synthetic or natural populations, or any other corn variety and which possess enhanced grain quality traits for pigment accmulation. Resulting hybrid kernels arising on the female corn plants will express enhanced grain quality traits which either increase or decrease the level of pigmentation to commercial advantage.

Corn varieties containing genes controlling the accmulation of kernel pigment are widely available for the public by commercial purchase or through numerous corn seed banks, principal among which is the Maize Genetics Cooperators Stock Center, University of Illinois, Urbana, Ill.

Taken together, Examples 1, 2 and 3 indicate hybrid kernels arising from cross-fertilization of high-oil and low-oil lines contain higher concentrations of oil than that found in the low-oil parent. This is true regardless of whether the male or female plants are themselves hybrid or inbred, and occurs whether the high-oil pollinators comprise members of synthetic populations, open pollinated varieties, or partial inbreds exhibiting varying degrees of genetic homogeneity. A wide variety of inbreds and hybrids exhibiting a range of oil concentrations can be combined by intermating to produce hybrid kernels which are significantly higher in oil content than those borne on the low-oil parent, and in many cases the oil content of the hybrid kernel approaches or even exceeds expected midparent values.

Examples 1, 2 and 3 broadly illustrate that inheritance of oil content in corn is subject to a xenia effect, whereby the oil quantity potential of the male gamete directly influences the oil quantity of F1 hybrid seed or grain. Since plants from two major populations exhibiting high oil, Illinois High Oil and Alexho Synthetic, can confer a high-oil content to F1 hybrid kernels, it is likely that new populations, subpopulations, varieties, hybrids or inbreds derived solely or in part from these populations will also exhibit xenia for oil. Several inbreds tracing their ancestry to either Alexho Synthetic or Illinois High Oil have been released to the public, including the inbreds R802A, R805 and R806 available from the Director of the Agricultural Experiment Station, University of Illinois, Urbana, Ill. Since oil in corn is inherited quantitatively, it is likely that most or all other high-oil varieties will exhibit a xenia effect for oil when so tested. Example 4 illustrates that the preferred high oil pollinator ASKC28 does significantly increase the oil content of hybrid kernels arising from the open pollination of a low-oil male sterile hybrid by male fertile ASKC28 plants. In this manner the method of this invention is demonstrated in its preferred form with respect to increased oil content as an enhanced quality grain trait. Note that ASKC28 used in Example 4 is not an agronomically improved variety, is not isogenic to the low-oil female corn hybride, is planted as a minor component of the entire corn population, and yet is effective in producing high-oil kernels both on itself and on an agronomically elite male sterile female parent. Kernels arising on each plant type could be harvested as grain to enter the stream of commerce.

Example 5 demonstrates that pollen arising on high-oleic corn plants when crossed onto low-oleic female corn plants will produce high-oleic hybrid kernels on the female corn plants. Three separate high-oleic corn inbreds are each effective in producing high-oleic hybrid kernels on the female corn plants. By analogy to Examples 1,2 and 3 it is probable that high oleic corn varieties when crossed at male onto low-oleic elite hybrid corn varieties used as female will produce high-oleic kernels or grain. Example 5 illustrates xenia imparting high-oleic content as an enhanced quality grain trait to hybrid kernels which could be harvested as grain when arising on agronomically elite hybrid female plants.

Example 6 demonstrates that pollen arising on members of the higher-protein synthetic population ASKC28 when crossed by open pollination onto the lower-protein elite hybrid Pfister 3000 ms as female plants gives rise to hybrid kernels exhibiting higher protein concentrations than that arising on Pfister 3000 following open pollination. By analogy to Example 4, Example 6 demonstrates the method of invention in preferred embodiment with respect to protein content as an enhanced quality grain trait. By analogy to Examples 1,2,3, and 5 it is probable that higher-protein varieties other than ASKC28 will exhibit xenia for protein concentration and can be used as pollinators onto a number of lower-protein varieties or hybrids produce higher lysine grain as described in the method.

Example 7 demonstrates that pollen arising on members of the higher-lysine synthetic population ASKC28 or on the higher lysine hybrids [LH119 X ASKC28] or X354 when crossed by open pollination onto the low-lysine elite hybrid Pfister 3000 ms gives rise to hybrid kernels with higher lysine contents when compared to the lower lysine female parent. By analogy to Examples 4 and 6, Example 7 demonstrates the method of the instant invention in its preferred embodiment with respect to increased lysine concentration as an enhanced quality grain trait. By analogy to Examples 1,2,3, and 5 it is probable that higher-lysine varieties other than ASKC28 will exhibit xenia for lysine concentration and can be used as pollinators onto a number of lower-lysine varieties or hybrids to produced higher lysine grain as described in the method.

Example 8 illustrates that kernels arising on low-amylose corn varieties following pollination by certain high-amylose corn varieties will give rise to high-amylose hybrid kernels. By analogy to Examples 4, 6 and 7 it is probable that hybrid kernels arising on a low-amylose elite hybrid female corn plants following open pollination by certain high-amylose corn varieties will themselves be high-amylose.

Example 9 illustrates that kernels arising on female corn plants pollinated by male corn plants expressing kernel pigment content as an enhanced grain quality trait will give rise to hybrid kernels containing pigment as an enhanced grain quality trait. By analogy to Example 4, 6 and 7 it is probable that hybrid kernels arising on female corn plants following open pollination by certain plants containing enhanced grain quality traits for pigment accumulation will themselves contain altered pigmentation as an enhanced grain quality trait.

Application of the xenia effect is a novel method for the production of corn grain with enhanced grain quality traits by farmers and commercial growers will ensure prompt availability of important corn products. Preferred, by virtue of its high yield of grain or its production of grain with enhanced quality grain traits, is a method consisting of planting a high-yielding F1 hybrid used as female corn plant which would be pollinated by plants containing genes for enhanced quality grain traits. The female hybrid would arise from crosses between a cytoplasmically male sterile inbred and a second inbred which would not restore fertility to the hybrid. Alternatively, the female plants-could be rendered male sterile by other methods, such as detasseling. The corn plants with genes for enhanced quality grain traits used as pollinators could be either inbreds, hybrids, varieties, synthetics or exotics or any other suitable germplasm source containing genes for enhanced quality grain traits which exhibit a xenia effect. The plants with genes for enhanced grain quality traits serving as pollinators could be interplanted with the hybrid female plants, or could be planted in rows alternating with rows containing only female hybrids. As grain with enhanced kernel quality traits would be obtained either by the selective harvest of grain arising on the female plant or, if advantageous, grain arising by self-pollination of plants serving as pollinators may also be harvested and blended with grain arising on the female plants.

When oil, protein, or lysine quantity is the enhanced quality grain trait of interest, most preferred would be the use of a high-yielding F1 hybrid as the female corn plant, ASKC28 as the nonisogenic variety serving as pollinator with random interplanting of the two types of plants followed by harvesting of the corn grain from all plants. When increased oleic acid content is the enhanced quality grain trait of interest, B73ol would be substituted for ASKC28 as the most preferred pollinator in the Method described above. When high amylose content is the quality trait of interest, Ae-5180 or a variety with similar characteristics would be substituted for ASKC28 as the most preferred pollinator in the method described above.

The instant invention differs significantly from current grain production methods in several important respects. Current grain production methods require that the inbred, hybrid, variety, population, or any other source of germplasm used as the source-for enhanced quality grain traits would exhibit high specific combining ability with elite parents to produce hybrid seed which would subsequently give rise to agronomically elite hybrid plants. This enhanced quality grain trait hybrid would then be planted in a grower's field and allowed to open pollinate to produce grain. Long, costly breeding programs are required to create inbreds which combine well preserving all beneficial traits including, for example, yield, disease resistance, stalk strength as well as quality grain traits under current practices. Under the claimed method the primary requirement of the enhanced quality grain trait parent serving as a pollinator would be that it sheds sufficient pollen to efficiently pollinate the high-yielding female plants. Most importantly, this novel method greatly reduces the breeding timeline and extensive effort necessary to develop the inbred pollinators required for commercial production of grain with enhanced quality traits. This is because the favorable agronomic properties key to successful grain production would already be embodied in the high-yielding hybrid employed as the female plants.

Because the instant invention eliminates many of the constraints placed on the performance of the parental lines necessary to support current grain production methods, it will allow a greatly accelerated introduction of corn grain with enhanced quality grain traits into the market place. Current agronomic practices can be utilized allowing the immediate production grain with a number of enhanced quality grain traits by commercial farmers.

Applicants' invention also differs significantly from current grain production methods in that the invention requires that the direction of pollination be specified. In contrast, in current grain production, open and random pollination occurs.

Applicants' invention differs most significantly from current hybrid grain production methods in that the invention permits the female corn plants be nonisogenic to the corn variety serving as pollinator. Current grain production methods involve open pollination among plants comprising a single hybrid variety in a grower's field or blends of male sterile and male fertile hybrids which are isogenic. In either case, in current grain production methods both female plants and pollinator plants are isogenic or are of the same variety. This is true whether field corn or speciality corn is being grown for grain production. The development of such isogenic materials requires extensive effort, expense, and time.

Finally, where oil content is the enhanced quality trait of interest, if the high-oil corn variety serving as the pollinator is genetically uniform (that is, substantially inbred or homozygous) the grain harvested under the claimed method my also be substantially uniform in oil content and overall grain quality. In contrast, F2 grain produced from F1 hybrid seed which is heterozygous for high-oil genes will differ in oil content from seed to seed due to the segregation of oil genes in commercial grain. Since increasing grain oil content is obligatorily associated with increased germ size, grain produced by the conventional method will segregate to some degree for overall kernel quality. Uniform grain quality is an important quality attribute of commercial value to the corn milling industry. By analogy, the uniformity of other enhanced quality grain traits may be similarly increased.

The instant invention or variants of that method will be applicable to the production of any specialty grain which relies on the expression of a kernel quality trait which exhibits a xenia effect. This would be true not only in corn but in any other crop that produces an endosperm including but not limited to sorghum, wheat, rye, triticale, rice, barley, oats, and the various millet genera.

Corn line X387 has been deposited under terms conforming to the Budapest Treaty in the American Type Culture Collection (ATCC), Rockville, Md. 20852-1776 on Nov. 14, 1990, and bears the ATCC accession number 40917. Corn line ASKC28 has been deposited under terms conforming to the Budapest Treaty in the American Type Culture Collection (ATCC), Rockville, Md. 20852-1776 on Sep. 19, 1991, and bears the ATCC accession number 75105. Corn lines X325, X326, X327, X338 and X354 have been deposited under terms conforming to the Budapest Treaty in the ATCC on Feb. 1, 1994 and have been assigned ATCC accession numbers 75661, 75662, 75663, 75664 and 75665 respectively. Corn line LP11 has been deposited under terms conforming to the Budapest Treaty in the ATCC on Feb. 8, 1994 and has been assigned ATCC accession number 75670. Corn lines Reid Yellow Dent (RYDHOC7), Ill. Iowa 2-Ear (RBS1OHOC4), Ill., Disease Oil (Syn DOC8), Ultra High Oil (UHOC1), and Ill. Stiff Stalk Synthetic (RSSSCH)C5) have been deposited under terms conforming to the Budapest Treaty in the ATCC on Feb 22, 1994 and have been assigned ATCC access numbers 75680, 75681, 75682, 75683 and 75684 respectively. Corn line Alexo Elite (AEC2) has been deposited under terms conforming to the Budapest Treaty in the ATCC on Mar. 16, 1994 and has been assigned ATCC accession number 75705. Corn line X124, has been deposited under terms conforming to the Budapest Treaty in the ATCC on Apr. 7, 1994 and has been assigned ATCC accession number 75730.

What is claimed is:

1. A method for producing corn grain with an enhanced quality grain trait comprising the steps of:
    (a) randomly interplanting in a field:
        (1) corn seed of a high-yielding and agronomically elite hybrid variety to obtain female corn plants wherein said female corn plants have been rendered male sterile by genetic methods; and
        (2) corn seed of a heterozygous and heterogeneous variety, enhanced in a quality grain trait selected from the group consisting of quantity of oil, protein, lysine, oleic acid, and amylose, which variety is nonisogenic to and does not exhibit good combining ability with said female corn plants and capable of serving as a pollinator, to produce plants enhanced in said quality grain trait;
    (b) permitting said corn plants enhanced in said quality grain trait to pollinate said female corn plants, wherein said quality grain trait is expressed in corn grain on said female corn plants by a xenia effect;
    (c) harvesting the resulting corn grain on all corn plants, thereby obtaining a high yield of corn grain enhanced in said quality grain trait for use as grain.

2. A method of claim 1 wherein said quality grain trait is the quantity of oil and said corn plants serving as pollinators are high-oil corn plants.

3. The method of claim 2, wherein the female corn plants are agronomically elite F1 hybrids of high yield, but are low in oil.

4. The method of claim 3 wherein the female corn plants are high in oil.

5. The method of claim 2, wherein the high-oil corn plants serving as pollinators are high-oil inbreds.

6. The method of claim 2, wherein the high-oil corn plants serving as pollinators are high-oil hybrids.

7. The method of claim 2, wherein the high-oil corn plants serving as pollinators comprise a population containing high-oil plants.

8. The method of claim 2, wherein the high-oil corn plants serving as pollinators comprise an open pollinated variety of high oil corn.

9. The method of claim 2, wherein the high-oil corn plants serving as pollinators are hybrids derived from a cross of standard field corn lines and a high oil corn plant selected from the group consisting of high-oil concentration inbreds, high-oil concentration hybrids, a population containing high-oil concentration plants, and an open pollinated variety of high oil corn.

10. The method of claim 7 wherein the high-oil corn plants serving as pollinators are member of the group consisting of Alexho Synthetic, Ultra High Oil, Alexho Elite populations, the Illinois versions of the Disease Oil, Iowa 2 Ear, Reid Yellow Dent, and Iowa Stiff Stalk Synthetic populations which have also been selected for high oil.

11. The method of claim 2 wherein said female corn plants are derived from seed of a high-yielding F1 hybrid and said high-oil corn plants capable of serving as pollinators are derived from seed of ASKC28.

12. A method according to claim 1 wherein the enhanced quality grain trait is protein.

13. A method according to claim 12 wherein the enhanced protein corn plants capable of serving as pollinators are members of the group consisting of ASKC28.

14. A method according to claim 1 wherein the enhanced quality grain trait is lysine.

15. A method according to claim 14 wherein the enhanced lysine corn plants capable of serving pollinators are members of ASKC28.

16. A method according to claim 1 wherein the enhanced quality grain trait is oleic acid.

17. A method according to claim 1 wherein enhanced oleic acid corn plants capable of serving as pollinators are members of the group consisting of Va35, LH24 and B73ol.

18. A method according to claim 1 wherein the enhanced quality grain trait is amylose.

19. A method according to claim 1, wherein the enhanced amylose corn plants capable of serving as pollinators express the gene Ae-5180.

20. A method for producing corn grain with an enhanced quality grain trait comprising the steps of:
    (a) randomly interplanting in a field:
        (1) corn seed of a high-yielding and agronomically elite hybrid variety to obtain female corn plants wherein said female corn plants have been rendered male sterile by genetic methods; and
        (2) corn seed of a heterozygous and heterogeneous variety, enhanced in a quality grain trait selected from the group consisting of quantity of oil, protein, lysine, oleic acid, and amylose, which variety is nonisogenic to and does not exhibit good combining ability with said female corn plants and is capable of serving as a pollinator to produce plants enhanced in said quality grain trait, wherein the ratio of corn seed of said heterozygous and heterogeneous variety enhanced in said quality trait to corn seed of a high yielding and agronomically elite hybrid variety is not greater than one to three;

(b) permitting said corn plants enhanced in said quality grain trait to pollinate said female corn plants, wherein said quality grain trait is expressed in corn grain on said female corn plants by a xenia effect;

(c) harvesting the resulting corn grain on all corn plants, thereby obtaining a high yield of corn grain enhanced in said quality grain trait for use as grain.

21. The method of claim 2 wherein said female corn plants and said high-oil corn plants capable of serving as pollinators are interplanted randomly within a row, and grain from both said female plants and said high-oil corn plants capable of serving as pollinators is harvested.

22. A method of claim 1 for producing corn grain with an enhanced quality grain trait wherein said corn seed of a heterozygous and heterozygous variety capable of serving as a pollinator is enhanced in a quality grain trait selected from the group consisting of protein, lysine, oleic acid, and amylose.

* * * * *